(12) United States Patent
Conlisk, Jr. et al.

(10) Patent No.: US 9,737,653 B2
(45) Date of Patent: Aug. 22, 2017

(54) SELECTIVE ULTRAFILTRATION MEMBRANES FOR RENAL REPLACEMENT THERAPIES

(76) Inventors: Albert Terrence Conlisk, Jr., Columbus, OH (US); Subhra Datta, Columbus, OH (US); William H. Fissell, Brecksville, OH (US); Shuvo Roy, San Francisco, CA (US)

( * ) Notice: Subject to any disclaimer, the term of this patent is extended or adjusted under 35 U.S.C. 154(b) by 349 days.

(21) Appl. No.: 13/195,774

(22) Filed: Aug. 1, 2011

(65) Prior Publication Data
US 2012/0310136 A1  Dec. 6, 2012

Related U.S. Application Data

(63) Continuation of application No. PCT/US2010/022687, filed on Feb. 1, 2010.

(60) Provisional application No. 61/148,833, filed on Jan. 30, 2009.

(51) Int. Cl.
| | | |
|---|---|---|
| *A61M 1/34* | (2006.01) | |
| *B01D 29/00* | (2006.01) | |
| *B01D 63/00* | (2006.01) | |
| *A61M 1/16* | (2006.01) | |
| *B01D 61/14* | (2006.01) | |
| *B01D 61/18* | (2006.01) | |
| *B01D 61/42* | (2006.01) | |

(52) U.S. Cl.
CPC .............. *A61M 1/16* (2013.01); *B01D 61/145* (2013.01); *B01D 61/18* (2013.01); *B01D 61/425* (2013.01); *B01D 2313/20* (2013.01); *B01D 2313/345* (2013.01)

(58) Field of Classification Search
None
See application file for complete search history.

(56) References Cited

U.S. PATENT DOCUMENTS

| | | | |
|---|---|---|---|
| 5,545,131 | A | 8/1996 | Davankov |
| 6,623,441 | B1 | 9/2003 | Kihara et al. |
| 7,048,856 | B2* | 5/2006 | Fissell et al. ................. 210/645 |
| 7,332,330 | B2* | 2/2008 | Humes et al. ............. 435/297.1 |
| 2002/0115956 | A1* | 8/2002 | Ross ............................ 604/6.04 |
| 2007/0119781 | A1 | 5/2007 | Huang et al. |

* cited by examiner

*Primary Examiner* — Tatyana Zalukaeva
*Assistant Examiner* — Sara Sass
(74) *Attorney, Agent, or Firm* — Standley Law Group LLP

(57) ABSTRACT

A system and method provide improved ultrafiltration of charged/uncharged solutes in a fluid, especially a body fluid. The improvement is achieved through imposed electric field and/or surface charge patterning to a permeable membrane. In many of the embodiments, at least one selected material is used as an additive on a permeate side of the permeable membrane to reduce the sieving coefficient of the membrane with regard to a solute present in the fluid.

20 Claims, 9 Drawing Sheets

Figure 1

(Prior Art)

| *8 nm* nanopore | | | *7 nm* nanopore | |
|---|---|---|---|---|
| | Surface pattern | | Surface pattern | |
| Zeta potential (*mV*) | Pattern A | Pattern B | Pattern A | Pattern B |
| -46 | 0.129 | 0.087 | 0.044 | 0.029 |
| -100 | 0.0105 | 0.01 | 0.001 | 0.001 |

| Quantity | Value |
|---|---|
| Temperature ($T$) | 300 K |
| Viscosity of water at $T = 300K$ | $0.00089 \, kg \cdot m^{-1} \cdot s^{-1}$ |
| Charge number of BSA in PBS at pH 7.4 | −15 |
| Stokes-Einstein Radius of Bovine Serum Albumin | 36 Å |
| Length of a membrane pore | 4 $\mu$m |
| Dielectric constant of water at $T = 300K$ | 78 |
| Transmembrane Pressure | 2 psi |
| Surface charge density on pore wall | $-0.01 \, C \cdot m^{-2}$ |

SELECTIVE ULTRAFILTRATION MEMBRANES FOR RENAL REPLACEMENT THERAPIES

CROSS-REFERENCE TO RELATED APPLICATIONS

This patent application is a continuation of and claims the benefit of priority from PCT/US2010/022687, filed 1 Feb. 2010, which is in turn entitled to the benefit of priority from U.S. Provisional Patent Application No. 61/148,833, filed 30 Jan. 2009. Each of the applications is hereby incorporated by reference in its entirety.

TECHNICAL FIELD

The disclosed embodiments are in the field of ultrafiltration, and more particularly in the field of selective filtration of charged/uncharged molecules potentially in biomedical and related applications.

BACKGROUND

Ultrafiltration is a membrane based filtration process of industrial and biological significance used to separate, purify and concentrate macromolecular solutions. In human physiology, the kidney performs ultrafiltration of blood through biological membranes located in nephrons, the functional units of the kidney. A related important application of ultrafiltration (using synthetic membranes) is to replace diseased kidney function using Renal Replacement Therapy (RRT) in patients suffering from Acute Renal Failure and End-stage-Renal Disease. Synthetic membranes are used to perform ultrafiltration in the food, water purification and pharmaceutical industries to name a few applications.

The replacement of renal function in persons with renal failure by dialysis is dependent on the ability to filter out waste products while preserving metabolically costly proteins, peptides and cells. Thus, there exists a need to maximize the retention of a large macromolecular solute of interest in the feed (supply) solution, and more specifically to improve the selectivity of current ultrafiltration systems. Examples of macromolecules of interest in this discussion are synthetic and natural proteins, carbohydrates, nucleic acids etc. with molecular dimensions of the order of and larger than 1 nm. Specifically, the retention of serum albumin in blood during ultrafiltration together with the clearance of middle molecules like $\beta_2$-microglobulin is not satisfactorily addressed in conventional therapies.

Diffusive transport of a molecule from one point in the fluid to another is proportional to the difference of concentrations of the molecule between the two points and is approximately inversely proportional to the molecular size, up to sizes excluded by the membrane. Thus, smaller molecules are extracted from, for example, blood more quickly than larger ones.

Conventional renal function replacement therapies often include membranes that have poor selectivity toward biologically important molecules or are too large for the possibility of patient implantation. The definition of membranes includes filtration devices utilizing well-defined pores as well as those utilizing a matrix of fibers. The former category includes membranes for industrial and therapeutic ultrafiltration and high flux dialysis; the latter category includes gels for gel permeation chromatography, the glomerular basement membrane and other extracellular matrices.

SUMMARY

This and other unmet needs of the prior art are met by devices and methods as described in more detail below.

A Renal Assist Device (RAD) employing ultrafiltration of blood (hemofiltration) can have a major impact on the cost of medical treatment of kidney failure. Dialysis is extremely expensive, time consuming, and stressful for the patient. The proposed method is superior to the prior art in hemofiltration because it significantly improves the solute retention capacity of the RAD through a nonintrusive and an inexpensive modification to the solution on the filtrate side of the membrane, rather than through costly re-design and repeated fabrication of the membrane, as required by competing nanofabrication technologies involving pore size reduction and/or surface charge modification. Disclosed method(s) may also significantly improve the capacity of ultrafiltration membranes to filter out solutes not only in implantable and extracorporeal renal replacement therapy applications, but also in food processing, pharmaceutical and waste-water-treatment applications.

The kidneys are paired organs, each similar in size to a clenched fist, that lie behind the abdominal cavity at the level of the bottom of the ribcage. In addition to their obvious role in waste excretion, the kidneys regulate multiple physiological processes essential to the health of the organism. In humans, the list of functions that kidneys accomplish include excretion of nitrogenous wastes and certain organic compounds, homeostasis of volume, osmolality, acid-base, divalent cations, phosphorus, and potassium; regulation of blood pressure and erythropoeisis, synthesis of Vitamin D, and, more controversially, antigen presentation, immunoregulation, and maintenance of redox balance. The kidney's filters ("glomeruli") are remarkable structures, in that the blood contains 40 gm/L of albumin, a globular protein important for health, and the filtered fluid in Bowman's space has mere micrograms of albumin per liter. Yet, the kidney's filters are able to pass other proteins and peptides, such as hemoglobin, myoglobin, and $\beta_2$-microglobulin that are only slightly smaller than albumin (12 kD-45 kD, compared to albumin's 66 kD).

The numerical calculations to be described in detail below predict that the solute-pore (albumin-pore) electrostatic repulsion results in a sieving coefficient (percent transported through the membrane) of 0.1% for a solute having a charge number characteristic of serum albumin at the physiological pH and ionic strength. It is found that higher surface charge density, smaller pore width and more complete surface coverage by charged surface-modification agent(s) leads to lower sieving coefficients. The selectivity of the membrane toward the charged solute also leads to concentration polarization.

Modification of pore wall surface charge is one strategy for improving the selectivity of a membrane toward solutes. The selectivity of a membrane to any particular solute is inversely proportional to the sieving coefficient to be defined below.

In general terms, the driving force for ultrafiltration is a pressure differential across the relevant membrane. This leads to a transfer, from the solution in the feed side (side F) toward the permeate side (side P), of solvent molecules and, of a fraction of the solute molecules on side F determined by a number of factors such as (a) the size, shape, charge of the pores/fibers, (b) the size, shape, charge, number density of the solute molecules, and (c) the filtration velocity.

A working equation that governs ultrafiltration applications with imposed electric field $E_x$ is:

$$S = \frac{(1+s)\phi_0 K_c}{1 - [1 - (1+s)\phi_0 K_c]\exp\left[-\frac{(1+s)K_c}{K_d}Pe\right]}$$

where S is the sieving coefficient, $\phi_0$ is the partition coefficient, $K_c$ is the hindered convection coefficient and Pe is the dimensionless Peclet number. The parameter s embodies the effect of electric field, being defined by $$s = \frac{zDE_x F K_d}{RT\bar{u}K_c}$$

where F is the Faraday's constant, R is the universal gas constant, T is the temperature, $E_x$ is the imposed electric field, z and D are the charge number and molecular diffusivity of the solute at the temperature of experiment, $K_c$ and $K_d$ are hindered convection and diffusion coefficients of the solute in the pore and $\bar{u}$ is the average velocity of the solvent within a slit-shaped pore of height 2 h due to the effect of applied pressure as well as voltages.

A small sieving coefficient is essential for the success of many ultrafiltration applications. For example, a sieving coefficient of 0.01% or lower for serum albumin is desirable for ultrafiltration-based renal replacement therapy. An example of embodiments of an ultrafiltration membrane employed as a bioartificial organ is presented in U.S. Pat. No. 7,048,856 to Fissell.

As mentioned above, the ultrafiltration performance of a membrane with respect to retention/passage of solute is usually characterized by the sieving coefficient S, defined as the ratio of the permeate side (the post filtration side) concentration $C_P$ of the solute (say in units of moles per liter) to the feed side (pre-filtration) concentration $C_F$ of the solute.

$$S = \frac{C_P}{C_F}$$

Here, feed and permeate refer to the solution to be filtered by the membrane (feed) and that already filtered through the membrane (permeate) on its downstream side.

One embodiment of the disclosed invention involves the use of additives in the permeate solution to affect the sieving coefficient, as defined above. The principles upon which the exemplary embodiments are quantitatively based are the fundamental concepts of equilibrium partitioning and hindered transport. The term equilibrium partitioning refers to the fact that the equilibrium concentration (in moles per liter of the solution) of a solute in a porous or fibrous media constituting the membrane is different from the equilibrium concentration in a bulk solution. For membrane transport, one can define two partition coefficients (a) the feed side partition coefficient $\phi_0$, and (b) the permeate partition coefficient $\phi_L$.

Formally, if a coordinate x is used to characterize distance across the pore of length L and if x=0 denotes the point immediately inside the membrane adjacent to the side F solution of concentration $C_F$ and x=L denotes a point immediately inside the membrane adjacent to side P having concentration $C_P$, then, the partition coefficients are defined by $$\phi_0 = \frac{C(x=0)}{C_F}$$

$$\phi_L = \frac{C(x=L)}{C_P}$$

Conventionally $\phi_0$ is equal to $\phi_L$.

The use of additives to affect the sieving of solutes, in the disclosed exemplary embodiments, utilizes the fact that the values of the partition coefficients, as defined above, may be tuned based on the concentration of dissolved solutes in the permeate side, thereby decreasing the sieving coefficient via the optimized addition of selected additives. The effect of additives on the sieving coefficient can be demonstrated as follows. If the partitioning coefficient $\phi_0$ is different from $\phi_L$, then, the sieving coefficient, S is given by:

$$S=\frac{\phi_0 K_c}{1-(1-\phi_L K_c)\exp\left(-\frac{K_c Pe}{K_d}\right)}$$

where $K_c$ is the hindered convection coefficient, $K_d$ is the hindered diffusion coefficient and $$Pe=\frac{\grave{o}vL}{D}$$

is the Peclet number which is a function of the porosity ò, filtration velocity v, diffusion coefficient D of the solute and L, the length (thickness) of the membrane.

In particular, in the small Pe limit, that is, as Pe approaches zero, which corresponds to purely diffusive equilibration between the permeate and feed solutions through the pore, $$S=\frac{\phi_0}{\phi_L}$$

A physical interpretation of the last equation is that any attractive/repulsive interaction in any part of the feed-pore-permeate system biases the Brownian motion of the solute molecules to redistribute more/fewer molecules in the zone of attraction/repulsion.

With respect to the effect of additives in the disclosed exemplary embodiments, it is important to note that (a) if $\phi_L$ increases, then the sieving coefficient decreases, as revealed by the last two equations for S, and (b) the concentration of additives can be used to affect a change in $\phi_L$. In particular, consider a permeate solution containing at least two dissolved ingredients: solute A and an additive B. The partition coefficient $\phi_L$ of solute A increases with increasing concentration of additive B, under certain conditions disclosed below.

Disclosed embodiments may involve the addition of varying amounts of, for example, large soluble charged/uncharged additive molecules B in the filtrate solution at the start/during the ultrafiltration that leads to an alteration in the value of $\phi_L$ for solute A. An increase in $\phi_L$ due to the addition of the additive B will result in a lower sieving coefficient S for solute A or improved selectivity. This in combination with other variables such as induced electric fields and/or surface coatings serve to greatly increase the selectivity (represented by sieving coefficient) of ultrafiltration membranes. For example, if the solute of interest is a large negatively charged species, a large negatively charged additive may be an appropriate choice for addition to the permeate solution. Its presence will likely increase the repulsive effects on the solute and thus reduce the sieving coefficient and prevent migration of the solute into the permeate.

BRIEF DESCRIPTION OF THE DRAWINGS

A better understanding of the exemplary embodiments will be had when reference is made to the accompanying drawings, wherein identical parts are identified with identical reference numerals, and wherein.

DETAILED DESCRIPTION

Figure 1:
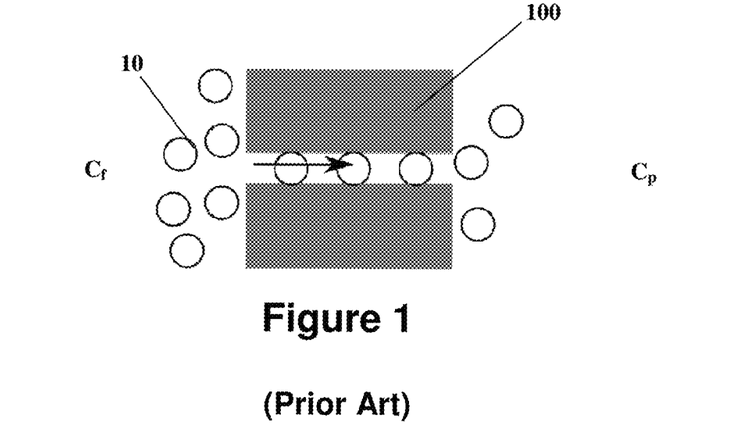
FIG. 1 is a schematic representation of an embodiment of a pore membrane.

FIG. 1 illustrates a conventional pore membrane filtration system. The solute particles 10 are allowed to distribute on either side of the membrane 100, their concentration difference (the difference between the concentration on the feed side and the concentration on the permeate side) only determined by size exclusion and rate of passage across the membrane. This arrangement generally is not highly selective.

Figure 2:
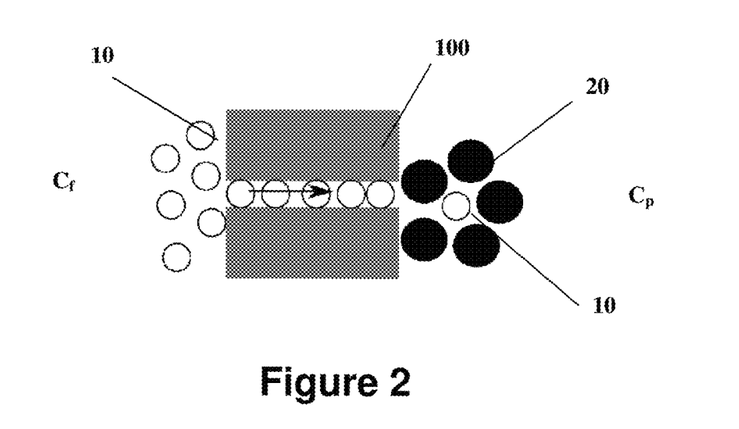
FIG. 2 is a schematic representation of an embodiment of a membrane pore with an additive added into the permeate solution.

In contrast to FIG. 1, is FIG. 2 which illustrates a pore membrane (similar to that of FIG. 1) and the concentration differential across it. This figure illustrates the scenario where the permeate solution contains at least two dissolved ingredients: a solute A 10 and an additive B 20. In this illustration, the partition coefficient $\phi_L$ of solute A increases with increasing concentration of additive B. More succinctly, an increase in $\phi_L$ due to the addition of additive B will result in a lower sieving coefficient for solute A or in other words, improved selectivity. The solute molecule represented on the right side of the drawing highlights the size exclusion properties relevant to disclosed embodiments. Additionally, if the additive 20 is appropriately paired with the relevant membrane 100 such that the membrane is impermeable to the additive (whether by size exclusion or other repulsive effects e.g. charge) then interaction with the solute will only occur on the permeate side of the membrane.

When a suitable additive is employed in the system the concentration differential may be decidedly altered. FIG. 2 shows a stark contrast in concentration of solute 10, when a suitable additive 20 is used. It is clear from the drawing that the additive further impedes the solute molecules from traversing the membrane pore. The additive may accomplish this through steric crowding of the pore exit alone. Additionally, the additive may have physico-chemical properties such a total molecular charge and charge distribution which cause intermolecular repulsion of the solute of interest. These properties will cause the solute to distribute more readily in the feed solution and membrane pore and significantly less in the permeate solution. Optionally, the membrane pore and additive may be selected such that the membrane is substantially impermeable to the additive.

Specific embodiments of the additive molecule include synthetically manufactured polysaccharides and proteins, biologically extracted polysaccharides and proteins. The solute A may comprise manufactured or biologically extracted proteins or other biologically active molecules. The solvents employed in the permeate side may include water, and organic solvents. The membrane may comprise either synthetic or biological membranes, but preferably should be highly impermeable to the additive of choice. Some particular characteristics of the additive may include: high solubility in the solvent of choice; a diameter that is sufficiently large relative to the average pore diameter to hinder passage, or, if a fibrous membrane is used, then larger than the average spacing between fibers; if the solute of interest possesses a molecular charge, the additive should preferably have a charge of the same sign as the solute.

An example of a suitable additive for use in improving membrane selectivity toward albumin is a dextran such as Dextran 500 (may be obtained from GE Life Sciences) or its sulfate salt. By means of example, Dextran 500 has a molecular weight close to 500,000 Da, and is readily soluble in water. The flexible polymeric structure of dextran leads to a large excluded volume; the solubility of dextran allows the use of higher concentrations to enhance repulsive interactions. Using Dextran 500 as an example of an embodiment of an additive for use in increasing the selectivity of a membrane toward a large negatively charged macromolecule of choice, Dextran has several important characteristics. The size of Dextran 500 molecules (~30 nm) will help to maintain a low probability of the additive entering an ultrafiltration membrane with sufficiently small pore sizes and fiber spacings (e.g. <10 nm) from the permeate solution, despite the flexibility of dextran. The optional use of dextran sulfate as additive B serves to electrostatically intensify the intermolecular repulsive interactions, when the solute is negatively charged (such as the protein serum albumin at physiological pH). The intermolecular repulsions between dextran (sulfate) and solute molecules in the permeate solution will lead to a higher $\phi_L$ (e.g. $C_p$ decreases) for the solute and consequently according to the equations above, an even lower sieving coefficient.

The partition coefficients of many macromolecular solutes are increasing functions of its own concentration and the concentration of other macromolecules present in the solution. The explanation for the above-discussed increase of partition coefficients is that, as the solution concentration(s) of similar/dissimilar macromolecule(s) increases, intermolecular repulsive interactions lead to a more significant reduction in the probability of a given solute molecule being located in the solution space more significantly than the probability for the same solute molecule being located in the pore/fiber-gap space. Herein, "repulsive intermolecular interaction" should be understood to include excluded volume effects.

Figure 3:
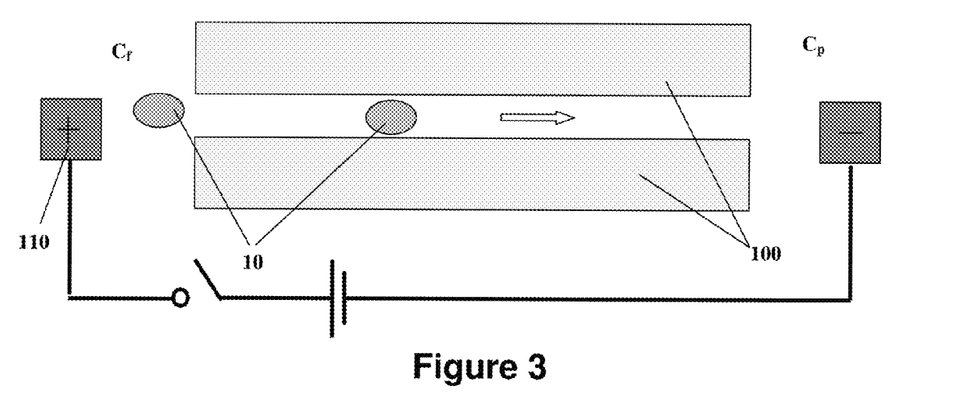
FIG. 3 is a schematic representation of a pore membrane incorporating an electric field.

FIG. 3 shows a membrane pore across which an electric field has been established, using a direct current source 110. According to equations above, when the electric field $E_x$ directed as shown in FIG. 3 is increased, S decreases for negatively charged solutes. In one embodiment of the application, a voltage of several tens to thousands of millivolts may be applied using the optional electrodes. In an embodiment wherein the solute 10 comprises a negatively charged species, as the electric field is employed in the manner represented in FIG. 3, the sieving coefficient will decrease, thus increasing the selectivity. This configuration has been demonstrated to produce sieving coefficients on the order of 0.01%.

Figure 4:
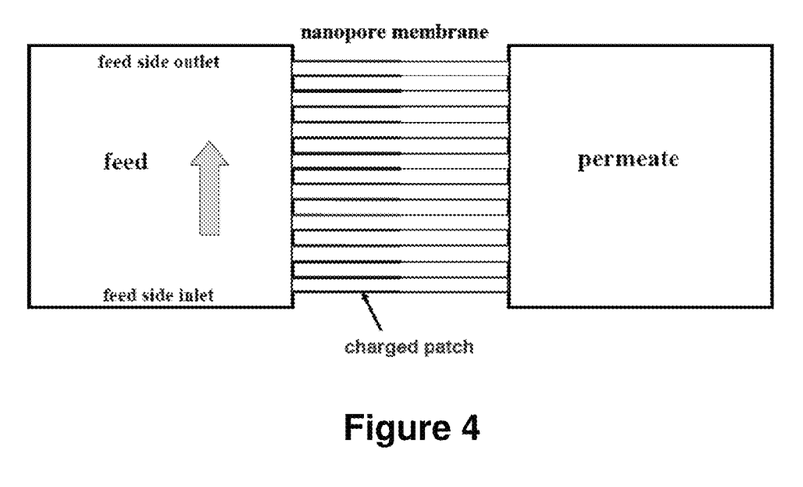
FIG. 4 shows the geometry of the feed-membrane-permeate system showing Pattern A patches. There are 8 nanopores of length 1 µm in the membrane.

Example calculations. The numerical simulation software COMSOL Multiphysics is used for the following calculation showing, how in one embodiment, appropriate patterning of surface charge on the pore walls can be used to enhance the selectivity to charged solutes. The geometry of the feed and permeate channels, the flow of the feed solution, and the nanopore membrane is shown in FIG. 4. All dimensions into the plane of the paper are large enough for the problem to be treated as two dimensional. The following parameters were used for the calculations. The length of the pores is 1 µm. The size of the feed and the permeate reservoirs is 10 µm by 10 µm. The feed channel flow distributes into 8 nanopores. The ionic strength of the electrolyte solution is 0.14 M. The concentration of the charged solute in the feed is 0.6 mM. The diffusion coefficient of the solute in the feed solution is $10^{-10}$ m$^2$/s. The solute is negatively charged and has a valence of 17. Two nanopore widths, viz. 8 nm and 7 nm are studied in this simulation. The dimensions of the feed and permeate channels are 10 µm by 10 µm. On the feed side, there is forced fluid flow moving perpendicular to the nanopores. The pressure at the feed inlet is assumed to be $p_o$=2 psi. Since the pressure drop on the feed side is negligible, the pressure at the outlet of the feed side is assumed to be 0.99 $p_o$. On the permeate side, the upper and lower boundary are both assumed to be open boundaries with pressure equal to zero. Two surface charge patterns are used. In Pattern A (shown in FIG. 4), a charged patch covers a fraction of the nanopore wall (the leftmost) and the remainder of the nanopore wall is uncharged. In Pattern B (not shown) the nanopore wall is completely covered by the charged patch or the patch length is 1 µm. For each patch pattern, the zeta potential or the surface charge further characterizes the patch. For example, in the following text, '−46 mV Pattern A patch' refers to a surface modification pattern where the zeta potential is −46 mV over the fraction covered by the patch and zero over the remainder of the pore wall. In all cases studied in this simulation, the patch length for Pattern A is 500 nm or 50% of the nanopore length.

Figure 5:
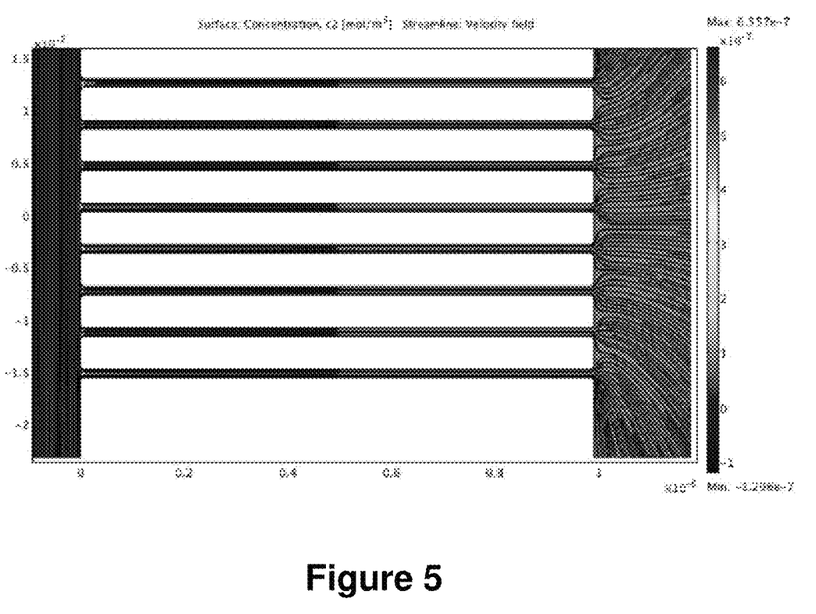
FIG. 5 is a streamline pattern for the flow of the feed solution for FIG. 4.

The results of the calculations are as follows. The feed side solution will be forced into the nanopores due to the pressure drop across the membrane. A −46 mV Pattern A patch is used. The streamline pattern for the flow of the feed solution is shown in FIG. 5. The total flow rate across the membrane is calculated to be 0.06% of the flow rate within the feed side. The concentration in the permeate channel is 0.077 mM and the resulting sieving coefficient is 0.128.

Figure 6:
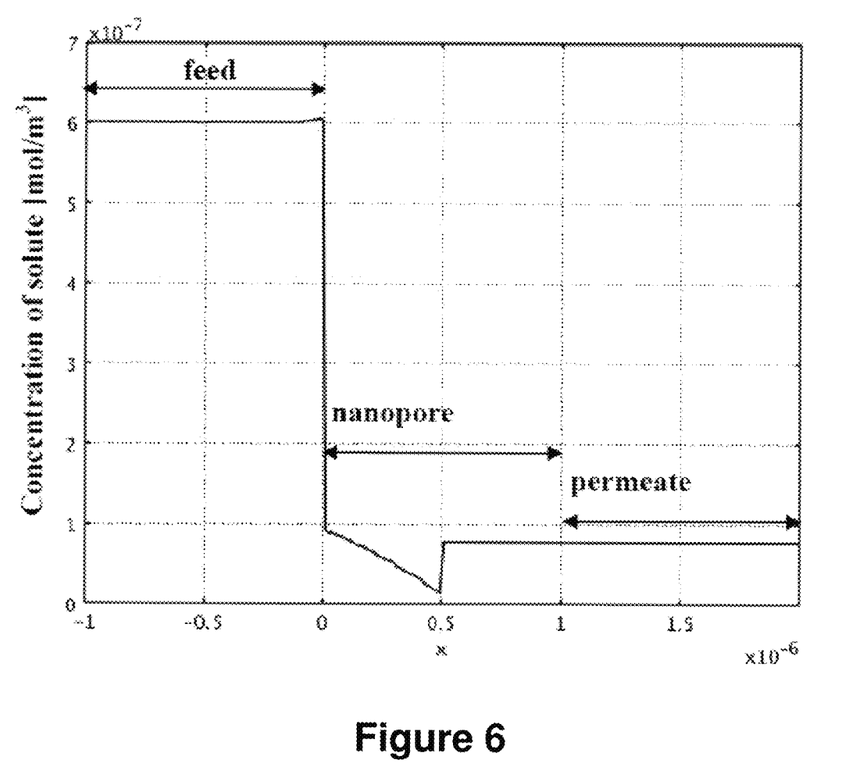
FIG. 6 shows the concentration of a charged solute at the center line of an 8 nm wide nanopore coated with a −46 mV Pattern A patch.
Figure 7:
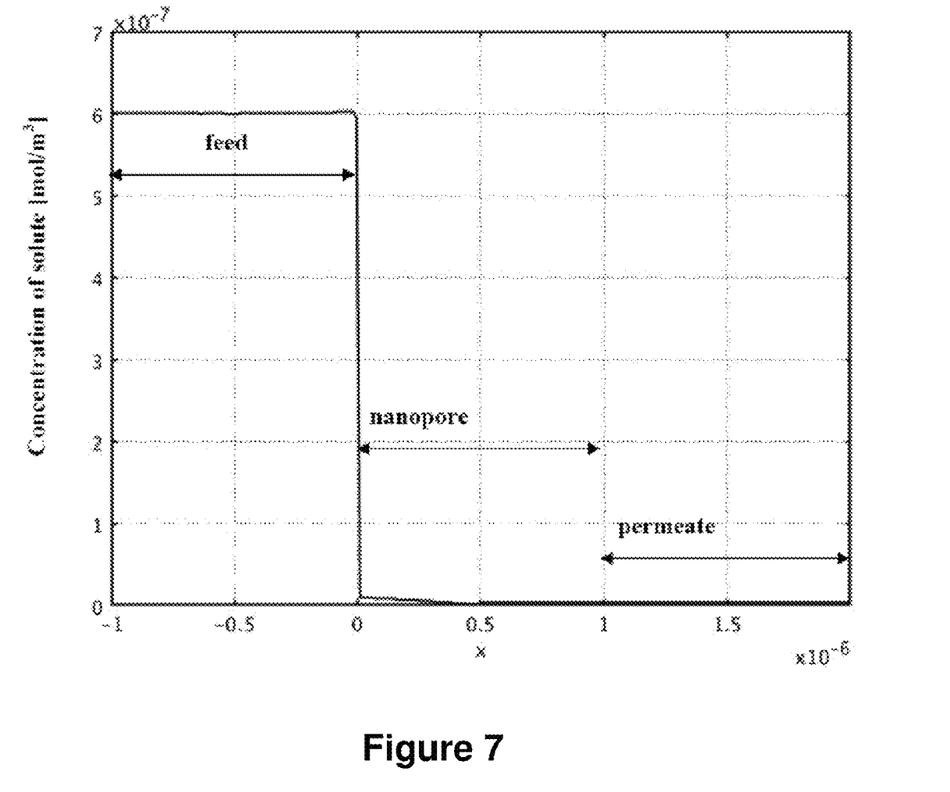
FIG. 7 shows the concentration distribution of a charged solute at the center line of an 8 nm nanopore coated with a −100 mV Pattern A patch.

The concentration polarization effect is evident in FIG. 6, as the concentration in the feed channel is higher near the membrane surface than in the bulk of the feed channel. Increasing the charge of the patch will significantly decrease the concentration of the charged species in the permeate channel. With a −100 mV Pattern A patch and an 8 nm wide nanopore, the sieving coefficient is 0.0105. The corresponding concentration distribution along the centerline of the nanopore is shown in FIG. 7.

Figure 8A:
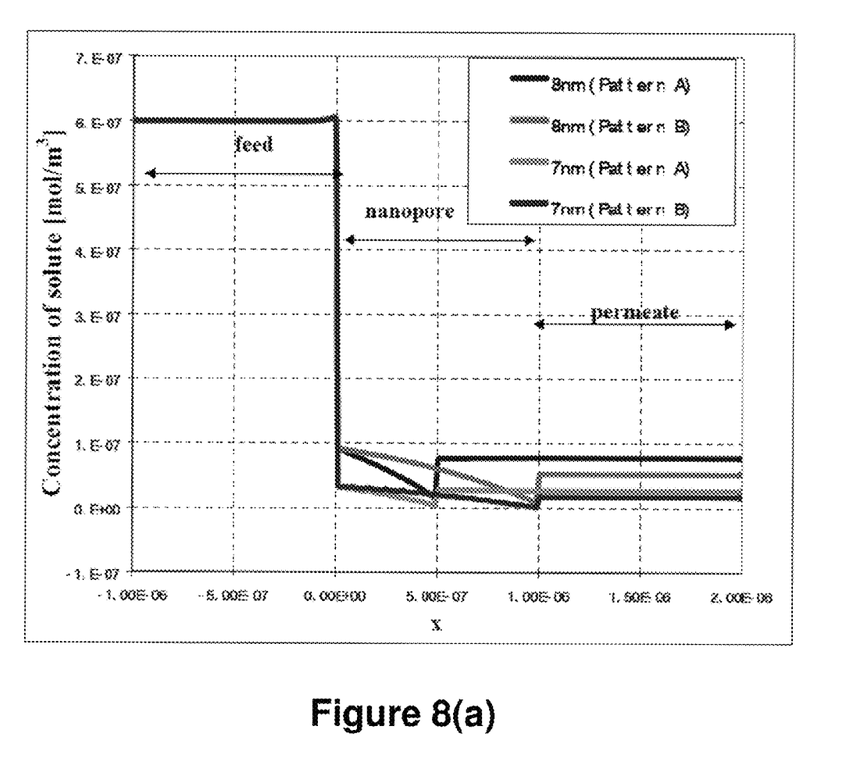
FIG. 8 shows the concentration distribution of a charged solute at the centerline of 8 nm wide nanopores coated with −46 mV patches of both Pattern A and Pattern B and a table for the resultant sieving coefficients.

In FIG. 8(a), the concentration at the centerline of the nanopore is plotted for 8 nm and 7 nm wide nanopores with a −46 mV charged patch. For smaller channels, the sieving coefficient is even smaller. The sieving coefficients corresponding to the four −46 mV patches in this figure are:

8 nm with Pattern A patch: 12.9%
8 nm with Pattern B patch: 8.7%
7 nm with Pattern A patch: 4.4%
7 nm with Pattern B patch: 2.9%

Figure 8B:
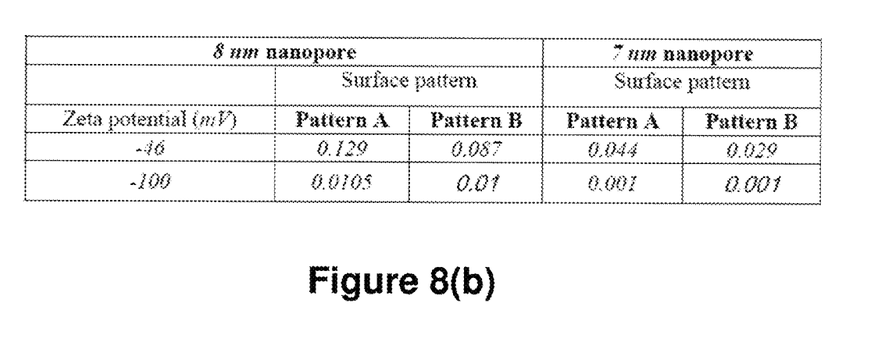

The sieving coefficient calculated for 8 nm and 7 nm wide nanopores are listed in FIG. 8(b) for two values −46 mV and −100 mV of the patch surface potential. Expectedly, the lowest sieving coefficient among the cases studied is obtained for the 7 nm wide nanopore and −100 mV patch. The solute selectivity is less sensitive to surface coverage (Pattern A or Pattern B) for the −100 mV patch.

Figure 9:
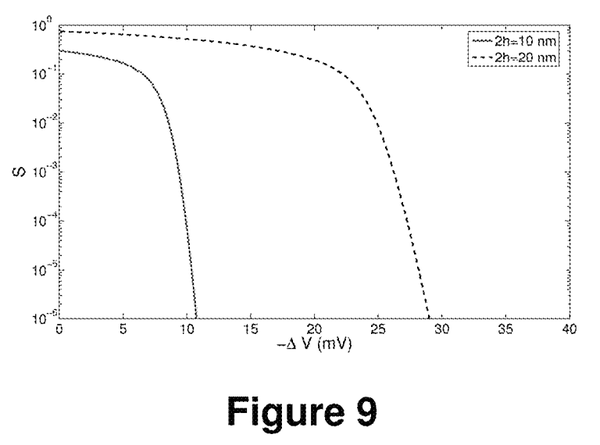
FIG. 9 is a plot of the calculated effect on the sieving coefficient of a pore of width 2 h after applying a voltage across the edge of the pore.
Figure 10:
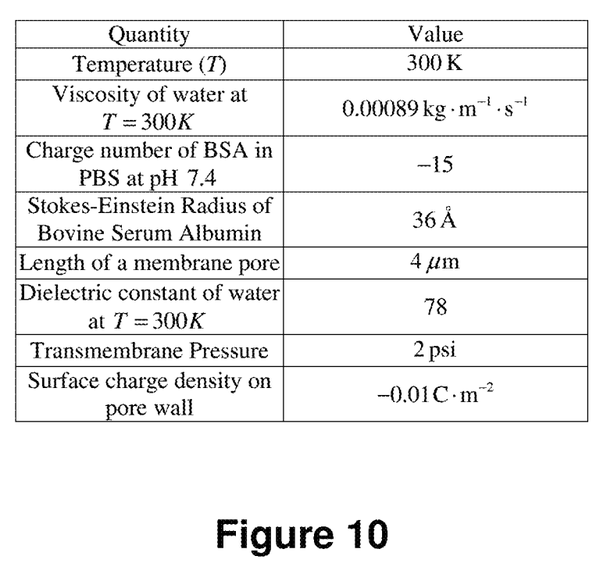
FIG. 10 is a table of values used for the calculations displayed in FIG. 9.

FIG. 9 using the parameters set out in FIG. 10 provides evidence of increasing the sieving coefficient by at least three orders of magnitudes for a solute of molecular size and electrical properties similar to bovine serum albumin with application of a modest voltage differential. A small sieving coefficient is essential for the success of many ultrafiltration applications. For example, a sieving coefficient of 0.01% or lower for serum albumin is desirable for ultrafiltration-based renal replacement therapy or a RAD.

In an embodiment, a first solute molecule is chosen and present in the feed solution, a suitably chosen second additive molecule is used in the permeate solution (side P); and the membrane is impermeable to the second additive molecule. In this case, the intermolecular interactions between the additive molecules and the solute molecules will take place only in the bulk solution on side P (permeate solution). In comparison to an ultrafiltration system where no such additive is added to the permeate solution, intermolecular repulsive interactions between the solute and additive will render the solute molecules less likely to locate in the bulk permeate solution, and, therefore, more likely to locate themselves inside the pore, increasing the permeate side partition coefficient $\phi_L$ for the solute. Moreover, the intermolecular repulsion can be made stronger by using a higher concentration of the dissolved additive.

Exemplary embodiments of the additive molecule B in the disclosed invention include but are not limited to synthetically manufactured or biologically extracted polysaccharides and proteins. Specific embodiments of the test molecule include but are not limited to synthetically manufactured or biologically extracted proteins and biological molecules. Exemplary embodiments of the solvent include but are not limited to water and organic solvents. Specific embodiments of the membrane include but are not limited to synthetic membranes and/or biological membranes either in vitro or in vivo. Specific applications for the operation of the membrane-based filter include, but are not limited to ultrafiltration, dialysis, and diafiltration.

In an embodiment, an ultrafiltration membrane (optionally comprising pores) separates two solutions, one the feed solution contains a solute of interest, the other, the permeate contains a separate solution. A suitable additive B is selected and employed at a suitable concentration, but is present only in the permeate side of the membrane. In this scenario, the intermolecular interactions between the additive and the solute of interest will take place only in the solution on the permeate side of the membrane. The result being that, in contrast to a system that employs no additive, repulsive intermolecular interactions between the solute and the additive will cause the solute molecules to locate more likely in the pore than in the permeate solution. In terms of the above referenced equations, the net effect is that $\phi_L$ is increased, thus decreasing the sieving coefficient. Optionally, the intermolecular repulsion may be increased by employing a higher concentration of the additive.

In an embodiment, the membrane employs in silica-based synthetic nanomembranes at physiological pH, this leads to an improvement in permeability (due to the phenomenon of electroosmosis) as well as selectivity, unlike conventional RAD technologies which involve trade-offs between permeability and selectivity. Further, no expensive surface modification step is required for the electrically enhanced RAD as compared to conventional methods and technologies that depend on repulsion between like charged walls and solutes to improve selectivity of the membrane. The membrane may be enhanced by the use of electrical fields and/or the introduction of selected additive molecules to the permeate solution prior to or during the filtration process.

Figure 11:
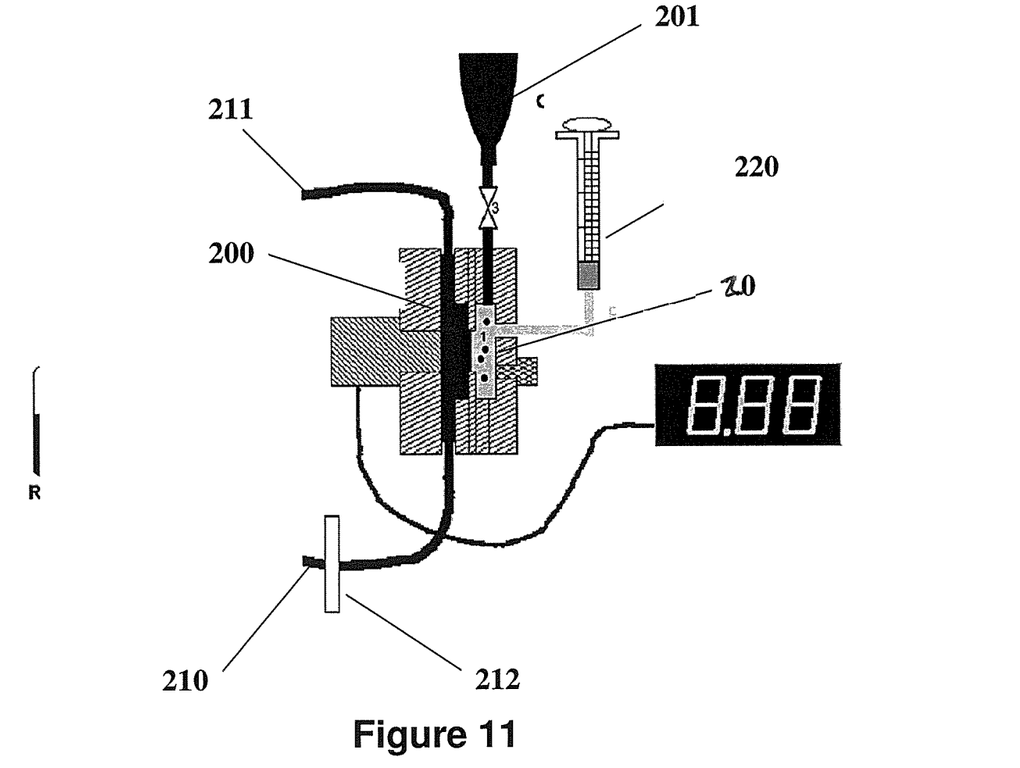
FIG. 11 shows a representation of an embodiment of a filtration system employing an additive to improve sieving coefficient.

FIG. 11 illustrates an embodiment of an ultrafiltration system employing a selected additive 20 to improve membrane selectivity. The system comprises a main filter chamber 200, a membrane inside the chamber. In this embodiment, the additive 20 is delivered to the permeate side by the addition apparatus 201, via tubing. The feed solution is delivered to the filtration chamber by tubing as well the tubing incorporating a feed line 210 and an exit opening 211, and is shown passing through optional prefilter 212 into the filtration chamber. The permeate solution is connected to a reservoir 220. Alternatively, the embodiment of FIG. 11 may include a membrane with an induced electric field to further improve selectivity of the membrane toward the solute of interest.

In an embodiment of a device employing an additive, a first solute molecule is chosen and present in the feed solution, a suitably chosen second additive molecule is used in the permeate solution (side P); and the membrane is impermeable to the second additive molecule. In this case, the intermolecular interactions between the additive molecules and the solute molecules will take place only in the bulk solution on side P (permeate solution). In comparison to an ultrafiltration system where no such additive is added to the permeate solution, intermolecular repulsive interactions between the solute and additive will render the solute molecules less likely to locate in the bulk permeate solution, and, therefore, more likely to locate themselves inside the pore, increasing the permeate side partition coefficient $\phi_L$ for the solute. Moreover, the intermolecular repulsion can be made stronger by using a higher concentration of the dissolved additive.

Specific embodiments of the additive molecule B in the disclosed invention include but are not limited to synthetically manufactured or biologically extracted polysaccharides and proteins. Specific embodiments of the test molecule include but are not limited to synthetically manufactured or biologically extracted proteins and biological molecules. Specific embodiments of the solvent include but are not limited to water and organic solvents. Specific embodiments of the membrane include but are not limited to synthetic membranes and/or biological membranes either in vitro or in vivo. Specific applications for the operation of the membrane-based filter include, but are not limited to ultrafiltration, dialysis, and diafiltration.

In an embodiment, an ultrafiltration membrane (optionally comprising pores) separates two solutions, one the feed solution contains a solute of interest, the other, the permeate contains a separate solution. A suitable additive B is selected and employed at a suitable concentration, but is present only in the permeate side of the membrane. In this scenario, the intermolecular interactions between the additive and the solute of interest will take place only in the solution on the permeate side of the membrane. The result being that, in contrast to a system that employs no additive, repulsive intermolecular interactions between the solute and the additive will cause the solute molecules to locate more likely in the pore than in the permeate solution. In terms of the above referenced equations, the net effect is that $\phi_L$ is increased, thus decreasing the sieving coefficient. Optionally, the intermolecular repulsion may be increased by employing a higher concentration of the additive.

Figure 12:
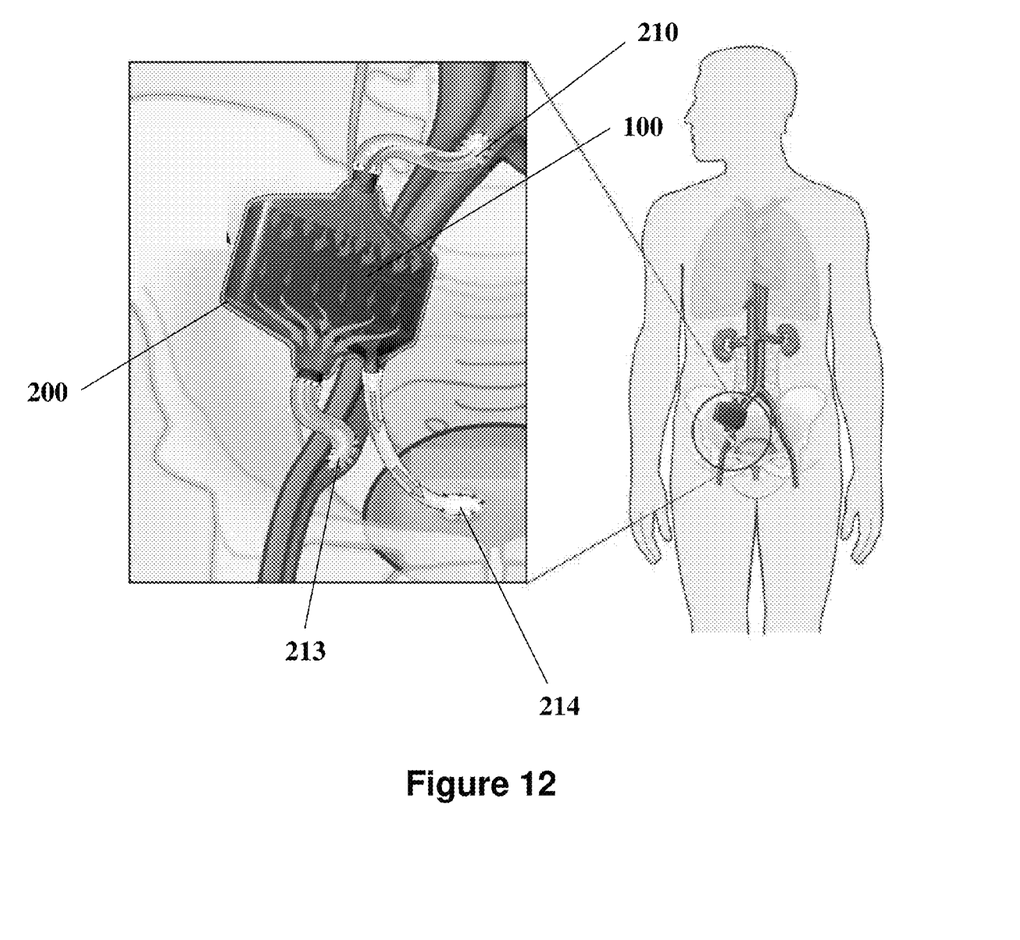
FIG. 12 shows an embodiment of an implanted Renal Assist Device.

In an embodiment, the membrane employs in silica-based synthetic nanomembranes at physiological pH, which leads to an improvement in permeability (due to the phenomenon of electroosmosis) as well as selectivity, unlike conventional renal replacement therapies which involve trade-offs between permeability and selectivity. Further, no expensive surface modification step is required for the electrically enhanced RAD as compared to conventional methods and technologies that depend on repulsion between like charged walls and solutes to improve selectivity of the membrane. The membrane may be enhanced by the use of electrical fields and/or the introduction of selected additive molecules to the permeate solution prior to or during the filtration process. A diagram of an embodiment of an implanted form of a RAD is shown in FIG. 12. The RAD may consist of a hemofiltration module and a cell bio-reactor module to replace the filtration and reabsorption tasks of a kidney, respectively. The final device may be a compact biocompatible cartridge handling afferent and efferent streams of blood and an exit stream that drains into the bladder.

Exemplary implantable embodiments comprise a main filter chamber 200 with a filter membrane, a feed line 210 for allowing a feed supply of fluid to enter the filter chamber on the feed side of the membrane, a permeate exit line 213 for reintroducing fluid into the body, and a waste exit line 214 for allowing filtered species to travel to, for example the bladder for elimination. The membrane may incorporate an electric field to increase selectivity as discussed above. Additionally, the permeate solution may contain a selected additive 20 chosen to improve the sieving coefficient of the membrane toward a solute 10 of choice. In an embodiment, the solute of choice is a large charged macromolecule such as albumin, and the additive is a dextran such as Dextran 500.

Having shown and described an embodiment of the invention, those skilled in the art will realize that many variations and modifications may be made to affect the described invention and still be within the scope of the claimed invention. Additionally, many of the elements indicated above may be altered or replaced by different elements which will provide the same result and fall within the spirit of the claimed invention.

What is claimed is:

1. A device for selective ultrafiltration of a fluid containing molecules of first and a second solute, by selectively retaining the first solute while passing the second solute, comprising:
a housing;
a main filtration chamber inside the housing;
an inlet port passing through the housing configured to receive the fluid;
an outlet port passing through the housing configured to return the fluid to a feed flow;
an ultrafiltration membrane contained in the main filtration chamber to divide the main filtration chamber into at least two interior chambers, a first of the at least two interior chambers being a feed chamber to contain the fluid and a second of the at least two chambers being a permeate chamber, the ultrafiltration membrane comprising pores sized to allow passage of the similarly-sized molecules and establish a sieving coefficient for each of the first and second solutes across the ultrafiltration membrane; and
a permeate solution, contained in the permeate chamber, the permeate solution comprising an additive solute that is selected so that the presence of the additive solute in the permeate solution decreases the sieving coefficient of the first solute across the ultrafiltration membrane relative to the sieving coefficient of the second solute across the ultrafiltration membrane, while the pores render the membrane substantially impermeable to the additive solute.

2. The device of claim 1, wherein:
the housing comprises a biocompatible material.

3. The device of claim 1, further comprising:
an electrode positioned for generating an electric field about a pore of the membrane.

4. The device of claim 1, further comprising:
a patterned pore wall surface charge.

5. The device of claim 1, wherein:
the housing is dimensioned for implantation in a human patient.

6. The device of claim 1, wherein:
the membrane comprises a silicon membrane.

7. The device of claim 1, wherein:
the additive solute is a charged macromolecule.

8. The device of claim 1, wherein:
the additive solute is selected to increase the selectivity of the ultrafiltration membrane by decreasing migration of a selected solute across the membrane.

9. The device of claim 8, wherein:
the additive solute is selected to decrease migration of serum albumin.

10. A method of selectively filtering solutes from a fluid, comprising the steps of:
providing a device according to claim 1;
delivering the fluid to the inlet port of the device;
passing the fluid across the membrane, effectively removing the selected solutes from the filtered fluid; and
removing the filtered fluid from the outlet port of the device.

11. The method of claim 10, wherein:
the filtered fluid is substantially devoid of proteins.

12. The method of claim 10, wherein:
the device further comprises an electrode positioned for generating an electric field about a pore of the membrane.

13. The method of claim 10, wherein:
the fluid being filtered is a biological fluid.

14. The method of claim 10, wherein:
the step of passing the fluid across the membrane occurs in vivo.

15. The method of claim 10, further comprising the step of:
delivering additive to the second chamber from time to time as required.

16. An implantable renal assist device comprising:
a housing, the housing including a first chamber and a second chamber,
the first chamber housing a feed fluid flow and the second chamber housing filtered permeate fluid;
a membrane separating the first chamber and the second chamber, the membrane comprising nanopores;
an inlet port passing through the housing into a first chamber configured to receive a fluid;
a first outlet port passing through the housing and out of the first chamber configured to return the fluid to a source flow;
a second outlet port passing through the housing and out of the second chamber configured to deliver filtered fluid to an elimination source;
an electrode positioned in communication with the membrane such that an electric field is generated about at least one pore; and
an additive solute, contained in the second chamber, selected to increase the selectivity of the ultrafiltration membrane by decreasing migration of a selected solute across the membrane, the membrane being substantially impermeable to the additive solute.

17. The device of claim 16, wherein:
the additive solute comprises a large macromolecule.

18. The device of claim 17, wherein:
the additive molecule is charged.

19. The device of claim 16, wherein:
the additive solute is selected to decrease migration of serum albumin across the ultrafiltration membrane.

20. The device of claim 1, wherein:
the first solute is serum albumin;
the second solute is $\beta_2$ microglobulin; and
the additive solute is dextran.

* * * * *

UNITED STATES PATENT AND TRADEMARK OFFICE
CERTIFICATE OF CORRECTION

PATENT NO. : 9,737,653 B2  
APPLICATION NO. : 13/195774  
DATED : August 22, 2017  
INVENTOR(S) : Conlisk, Jr. et al.

Page 1 of 1

It is certified that error appears in the above-identified patent and that said Letters Patent is hereby corrected as shown below:

In the Specification

Column 1, Line 14 (approx.), before the section heading "TECHNICAL FIELD" please add: "STATEMENT REGARDING FEDERALLY SPONSORED RESEARCH OR DEVELOPMENT This invention was made with government support under grant number EB008049 awarded by the National Institutes of Health. The government has certain rights in the invention."

Signed and Sealed this  
Fourth Day of August, 2020

Andrei Iancu  
*Director of the United States Patent and Trademark Office*